US012109016B2

(12) United States Patent
Ertelt

(10) Patent No.: US 12,109,016 B2
(45) Date of Patent: Oct. 8, 2024

(54) METHOD AND SYSTEM FOR GAIT ANALYSIS

(71) Applicant: MCG MOTION CAPTURE GMBH, Heidelberg (DE)

(72) Inventor: Thomas Ertelt, Berlin (DE)

(73) Assignee: MCG motion capture GmbH, Heidelberg (DE)

( * ) Notice: Subject to any disclaimer, the term of this patent is extended or adjusted under 35 U.S.C. 154(b) by 380 days.

(21) Appl. No.: 17/255,904

(22) PCT Filed: Jun. 28, 2019

(86) PCT No.: PCT/EP2019/067401
§ 371 (c)(1),
(2) Date: Dec. 23, 2020

(87) PCT Pub. No.: WO2020/002635
PCT Pub. Date: Jan. 2, 2020

(65) Prior Publication Data
US 2021/0186377 A1  Jun. 24, 2021

(30) Foreign Application Priority Data

Jun. 29, 2018 (EP) .................................... 18180924

(51) Int. Cl.
*A61B 5/11* (2006.01)
*A61B 5/103* (2006.01)
*A61B 5/00* (2006.01)

(52) U.S. Cl.
CPC ............ *A61B 5/112* (2013.01); *A61B 5/1038* (2013.01); *A61B 5/7267* (2013.01)

(58) Field of Classification Search
CPC ....... A61B 5/1118–1128; A61B 5/1036; A61B 5/1038; A61B 5/7235–7267
See application file for complete search history.

(56) References Cited

U.S. PATENT DOCUMENTS

| | | | |
|---|---|---|---|
| 2009/0240171 A1 | 9/2009 | Morris Bamberg | |
| 2016/0324445 A1 | 11/2016 | Kim et al. | |
| 2019/0150796 A1* | 5/2019 | Fukushi | ................. A61B 5/112 |

FOREIGN PATENT DOCUMENTS

| | | |
|---|---|---|
| EP | 0603115 A2 | 6/1994 |
| GB | 2549513 A | 10/2017 |

OTHER PUBLICATIONS

Okut, H. "Bayesian regularized neural networks for small n big p data." Artificial neural networks-models and applications: Ch 2. 28-48. (Year: 2016).*

(Continued)

*Primary Examiner* — David J. McCrosky
(74) *Attorney, Agent, or Firm* — QUARLES & BRADY LLP

(57) ABSTRACT

The invention relates to a method for gait analysis. In this method, data comprising a ground reaction force curve is first obtained from a force measuring device. Then, a determination of a first approximation of the ground reaction force curve performed by at least a first approximation function defined by a set of coefficients. Then, a determination of a second approximation of the ground reaction force curve is performed by a second approximation function formed on the basis of the set of coefficients of the at least one first approximation function. Further, the invention relates to a gait analysis system.

10 Claims, 2 Drawing Sheets

(56) References Cited

OTHER PUBLICATIONS

Jin, et al. "Wavelet basis function neural networks for sequential learning." IEEE Transactions on Neural Networks 19.3: 523-528. (Year: 2008).*
Savelberg, et al. "Assessment of the horizontal, fore-aft component of the ground reaction force from insole pressure patterns by using artificial neural networks." Clinical Biomechanics 14.8: 585-592. (Year: 1999).*
Alaqtash, M., et al. "Automatic classification of pathological gait patterns using ground reaction forces and machine learning algorithms." 2011 Annual International Conference of the IEEE Engineering in Medicine and Biology Society. IEEE, 2011.
Ertelt, T. Kraftmorphologie der menschlichen Beinbewegung: elektromyografische und kinematische Einflüsse frequenzbedingter Schlittensprünge. Hamburg, Verlag Dr. Kovac, 2008.
Ertelt, T. Translation of Introduction and section 2.4.7 of Kraftmorphologie der menschlichen Beinbewegung: elektromyografische und kinematische Einflüsse frequenzbedingter Schlittensprünge. Hamburg, Verlag Dr. Kovac, 2008.
European Patent Office. Extended European Search Report for application 18180924.5. Mailed on Jan. 3, 2019.
International Preliminary Report on Patentability for application PCT/EP2019/067401. Mailed Dec. 29, 2020. With translation.
International Searching Authority. International Search Report and Written Opinion for application PCT/EP2019/067401.Mailed on Aug. 26, 2019. With translation.

* cited by examiner

METHOD AND SYSTEM FOR GAIT ANALYSIS

CROSS-REFERENCE TO RELATED APPLICATIONS

This application is a U.S. National Stage of PCT Application No. PCT/EP2019/067401 filed on Jun. 28, 2019 which claims the benefit of priority to European Application No. 18180924.5 filed on Jun. 29, 2018, which are herein incorporated by reference in their entirety.

TECHNICAL FIELD

The invention relates to a method and a system for gait analysis. This may in particular be based on a kinetic observation.

TECHNICAL BACKGROUND

Gait analysis examines a person's natural mode of locomotion, namely walking and running. In a kinetic observation, this is usually done by measuring the ground reaction force, which is a reaction force of the ground to the force that the body transfers to the ground through the feet when stepping.

The qualitative and/or quantitative description of a ground reaction force finds application in, for example, medicine, biomechanics, robotics etc. Particularly in clinical applications, this can be used to show stresses, risks and pathological abnormalities or changes, especially as a result of diseases or injuries (acute and chronic). In sports medicine, as well as in clinical applications, gait is also used as an indicator of possible stress risks, as well as for assessing and clarifying existing impairments of patients, or as a measure of the success of a therapy.

An elementary parameter in the diagnostic area is the temporal course of the ground reaction force, which is usually classified visually and is therefore highly dependent on the experience
AO:TE
and knowledge of a diagnostician. Due to the complexity of the ground reaction force curve and numerous influencing parameters, in addition to the experience of the diagnostician, particular reference is made to individual characteristic parameters of the ground reaction force. For the vertical ground reaction force, these include a maximum force, a point in time of the maximum force, a ground contact time and for the horizontal ground reaction force a maximum acceleration, maximum deceleration, a net acceleration, etc. From these parameters, further characteristics can be determined, such as impulse/force impact, symmetries, etc. Despite these characteristic parameters and parameters, however, it is not yet possible to objectify the description of the ground reaction force curve, so that misjudgments can occur.

An approach to better objectification can be found for example in Alaqtash, M., Sarkodie-Gyan, T., Yu, H., Fuentes, O., Brower, R. & Abdelgawad, A. (2011). Automatic classification of pathological gait patterns using ground reaction forces and machine learning algorithms. Here, ground reaction forces of stroke patients are classified based on the characteristic parameters or parameters by a machine learning algorithm. The disadvantage of this is that the entire ground reaction force curve is not considered and analyzed, so that the method proposed for stroke patients cannot be transferred to other fields.

SUMMARY

It is therefore the object of the invention to provide an improved possibility for gait analysis with the highest possible objectivity.

The object is solved by the subject-matter of the independent claims. Advantageous further embodiments of the invention are indicated in the dependent claims, the description and the accompanying drawings.

A first aspect provides a method for gait analysis. The method may be performed, for example, by means of a data processing device, which may comprise a processor, a memory, and optionally an interface for a measuring device, etc. The method may be stored as computer program instructions in the memory to be executed by the processor, and may comprise the following steps:

First, data is obtained from a force measuring device that includes a ground reaction force history, that is, a ground reaction force over a period of time. The force measuring device may be connected to the data processing system and thus directly provide the data. Alternatively, the data may be transmitted via a data or network connection or may be temporarily stored on a data storage medium. The data may be normalized to the body weight of a person whose gait is to be analyzed for better comparability. Accordingly, the ground reaction force may be expressed as a percentage of body weight. In analyses relating to gait, for example walking and running, the force curve to be described may be limited to a contact time between a foot and the ground or the force measuring device. In an analysis with a different focus, such as a task for balance, jumping, stopping or side-stepping maneuvers, the range considered may also be limited to a time window.

Then, a determination of a first approximation of the ground reaction force curve is performed by at least a first approximation function defined by a set of coefficients.

Based on the set of coefficients of the at least one first approximate function, a second approximation of the ground reaction force curve is then determined by a second approximate function, the second approximate function being formed by a combination of the coefficients.

In other words, a selected section of force, in this case the ground reaction force curve, is approximated in order to describe this measured curve as objectively as possible with the best possible matching.

With this configuration, the invention offers several advantages. This provides a possibility to objectify the gait analysis and, in particular, to achieve a quantifiable description independent of a diagnostician. Uniform interventions and strategies can be derived from the gait analysis according to the invention, for example also for possible surgical interventions as well as therapeutic and rehabilitative measures.

In an embodiment, the at least one set of coefficients may be combined in a coefficient pool from which individual coefficients may be combined to form the second approximation function. The more first approximation functions are determined, the more sets of coefficients are combined in the coefficient pool and are available for the second approximation. By selecting individual coefficients from the coefficient pool, the ground reaction force curve can be described exactly.

According to an embodiment, a plurality of mutually different first approximation functions may be determined, which are defined by the respective set of coefficients. The first approximation functions may differ, for example, only in one of a plurality of coefficients. All coefficients can be combined in the coefficient pool described above. By being able to select from several sets of coefficients, the second approximation can be performed with high accuracy.

In an embodiment, it can be provided that at least two first approximation functions are selected iteratively, from which a sum function and its deviation from the ground reaction force curve are determined in a respective iteration step until the deviation reaches a predetermined termination criterion and the corresponding first approximation function for the first approximation is determined therefrom. For example, residuals, i.e. the sum of the deviations squared, may be determined from the sum function of the selected first approximation functions. By squaring, small deviations can be attenuated in their effect and large deviations, for example deviations>1, can be amplified. This selection or adjustment can be repeated until a minimum of the residuals is given and the quality of the function reaches an $R^2$ of at least 0.8, for example. The minimum of the residuals, the values of the $R^2$ or a combination of both can be the termination criterion. The first approximation functions corresponding to this termination criterion can then be used for determining the second approximation by the second approximation function. Thus, with comparatively little computational effort, a good first approximation is obtained as a good starting point for the second approximation.

According to an embodiment, the coefficients forming the second approximation function may be compared in advance with at least one predetermined data set, which may comprise a plurality of classified ground reaction force trajectories, and validated therefrom whether the coefficients enable the second approximation. In other words, the selected first approximation functions or coefficients can be validated in a kind of training set. For this purpose, existing ground reaction force curves are first distinguished from each other on the basis of, for example, a visual analysis. It may be known, e.g. by observation and an assignment to a running style or the like, by findings from the literature, etc., which pattern of a ground reaction force curve corresponds to a certain running style. It can then be checked, using the training set, whether it is statistically possible to actually distinguish a predetermined class, e.g. a particular running style. For example, visually classified patterns can be assigned a known category, the differentiation of which is tested in a training set.

In an embodiment, the second approximation function is iteratively formed from the validated coefficients and the second approximation is assigned to a class. In other words, information can be obtained about the data set about a coefficient expression as a function of a classification group, such as running style, sport, pathology the like. These validated coefficients can now be used to obtain the best possible match with the ground reaction force curve to be analyzed. That is , a registered ground reaction force curve can be approximated based on the available coefficients. A termination criterion can be a minimization of the residual. It is now also known which basic characteristic the coefficients have in a respective class, so that the class can be determined for the ground reaction force curve with a corresponding probability.

According to an embodiment, the first approximation function can be a normal distribution or Gaussian function. These can be determined easily and have a low complexity. Nevertheless, a good first approximation can be achieved.

An embodiment provides that the second approximation function can be a sum function of the at least one first approximation function. This can be formed easily and allows, e.g. via a residual as a termination criterion, an iterative approximation with low computational effort.

In an embodiment, the set of coefficients may comprise a maximum value, a mean value, and/or a width of the first approximate function. In other words, each first approximate function may comprise three coefficients. This allows, for example, a normal distribution or Gaussian function to be fully defined.

According to an embodiment, a number of the determined first approximate functions may be set between 1 and 20, preferably between 1 and 15, more preferably to exactly 8. For example, the first approximate functions may be defined by three coefficients, so that for two first approximate functions I give 2·3=6, for three first approximate functions I give 3·3=9, etc. coefficients result. It has been shown that for a clinical application of gait analysis, particularly good results for describing the ground reaction force curve can be obtained with eight first approximate functions, i.e. 8·3=24 coefficients. However, depending on the complexity, 15 or more first approximate functions can also be determined. Surprisingly, however, it has been shown that with eight first approximation functions a good quality of approximation can be achieved with comparatively low computational effort.

A second aspect provides a gait analysis system. This may be implemented by means of a data processing device and is preferably arranged to perform the method described above in one or more embodiments. The gait analysis system comprises:

A force measuring device adapted to detect a ground reaction force. This may comprise, for example, a force plate, an instrumented treadmill, instrumented insoles or the like. For example, an insole for a shoe may comprise a plurality of individual sensors, such as foil-based sensors, which may preferably be arranged at anatomically relevant points or portions of a foot interacting with the insole. In a further embodiment, for example, 8 to 25, preferably 12 to 20, further preferably 14 to 18, particularly preferably 15 to 16, individual sensors may be provided distributed over a planar extension of the insole. The individual sensors can provide individual signals, in particular in the form of a deflection and/or peak, as a result of a force acting thereon, the sum of the individual signals providing an overall signal of the ground reaction force. This overall signal can be approximated, for example, by a combination of coefficients as explained in the method described above. Alternatively to the combination of coefficients, it is possible to determine only the deflection and/or peak, which may be approximately comparable to an amplitude of a Gaussian function or Gaussian curve, and a time point, in particular an absolute or relative time point, which may be approximately comparable to a position of a Gaussian function or Gaussian curve. A width of the distribution may be determined in this case by a determination of a standard deviation about the time function. This results, for example, in three coefficients from which an approximation can be determined. Due to a reduced amount of data, this determination can, for example, be carried out directly by an electronic evaluation device which can be integrated into the insole or form an assembly with the same.

An electronic evaluation device which may comprise, for example, a processor and a memory, and which is arranged to, approximate the sensed ground reaction force curve by at least a first approximation function defined by a set of coefficients, and to further approximate the ground reaction force curve by a second approximation function formed on the basis of the set of coefficients.

This creates a possibility to objectify the gait analysis and in particular to achieve a quantifiable description independent of a diagnostician.

According to an embodiment, the gait analysis system may further comprise a database which may be arranged to assign a combination of coefficients forming the second approximation function to a predetermined gait behavior and/or a gait abnormality. For example, the database may comprise the predetermined data set described above and may be arranged to validate and/or classify the coefficients using the data set, in particular by the evaluation means.

In an embodiment, the gait analysis system may further comprise at least one neural network arranged to obtain at least the coefficients as an input variable and to generate class information as an output variable. In a further embodiment, the termination criterion may additionally represent a further input variable. The neural network may be multilayer and/or convolutional, wherein the coefficients are supplied to an input layer and the class information, for example running style, sport, pathology or the like, is output from the output layer. The neural network may comprise, for example, a Bayesian Regularization Artificial Neural Network (BRANN). This provides high robustness with respect to training and/or validation, and the neural network may preferably take into account the termination criterion for the approximation. The output variable may be a respective sport, in a medical setting possibly the respective pathology or stage of impairment. The neural network can detect even gradual differences between the individual coefficients and patterns, even in the case of very complex ground reaction force curves, and can therefore be advantageous over statistical methods such as discriminant or cluster analyses.

A third aspect provides a computer program element. This, when executed by means of a processor of an electronic evaluation device, causes the evaluation device to perform, for example, the method described above in one or more embodiments. In particular, it causes the following steps to be carried out:

obtaining data containing a ground reaction force curve from a force measuring device, determining a first approximation of the ground reaction force curve by at least a first approximation function defined by a set of coefficients, and determining a second approximation of the ground reaction force curve by a second approximation function formed on the basis of the set of coefficients of the first approximation function.

The resulting advantages are described above for the method as well as the gait analysis system.

A fourth aspect provides a computer-readable medium having stored thereon the computer program element described above.

BRIEF DESCRIPTION OF THE FIGURES

Embodiments of the invention are explained below with reference to the accompanying figures. Showing.

The figures are merely schematic representations and serve only to explain the invention. Identical or similar elements are provided throughout with the same reference signs.

EMBODIMENTS OF THE INVENTION

Figure 1:
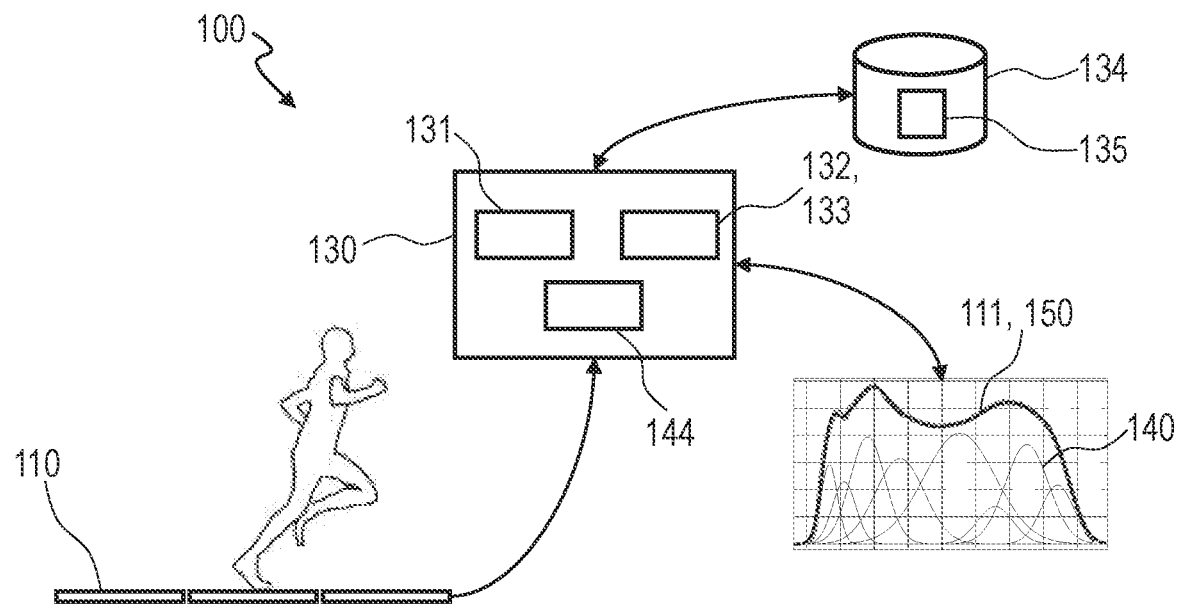
FIG. 1 a gait analysis system according to the invention, which is suitable for carrying out a gait analysis method according to the invention, FIG. 2 an exemplary ground reaction force curve with its first and second approximation, FIG. 3 an exemplary first approximation function defined by three coefficients, and FIG. 4 a flow chart of a gait analysis method according to the invention.

FIG. 1 shows a schematic structure of a gait analysis system 100, which is particularly suitable for indicating stresses, risks and pathological abnormalities or changes, in particular as a result of illness or injury.

The gait analysis system 100 comprises a force measuring device 110 for measuring a ground reaction force over a period of time, i.e., a ground reaction force curve 111. In an exemplary embodiment, the force measuring device 110 is a force plate and provides electronic data that includes the ground reaction force curve 111. However, in some embodiments, the force measuring device 110 may also be formed by an insole for a shoe, which may include a plurality of individual sensors. For example, 10 to 25 individual sensors may be distributed over a planar extent of the insole, each providing an individual signal, for example in the form of a deflection and/or peak. Furthermore, the gait analysis system 100 has an electronic evaluation device 130, which has a processor 131 and a memory 132 and is set up to receive the data from the force measuring device 110, for example via a data interface. For example, the electronic evaluation device 130 may also be integrated in an insole for a shoe. The memory 132 stores program instructions or a program element 133 that can be executed by the processor 131 and in which at least one artificial intelligence module and/or a neural network having an input layer, one or more intermediate layers and an output layer is implemented. Preferably, the neural network may comprise or be a Bayesian Regularization Artificial Neural Network (BRANN). The evaluation device 130 further comprises or is connected to a database 134 for data exchange. In the database 134, at least one predetermined data set 135 comprising comparison data is available for evaluating or classifying the ground reaction force curve 111, so that an evaluation can be performed as automatically as possible.

Figure 2:
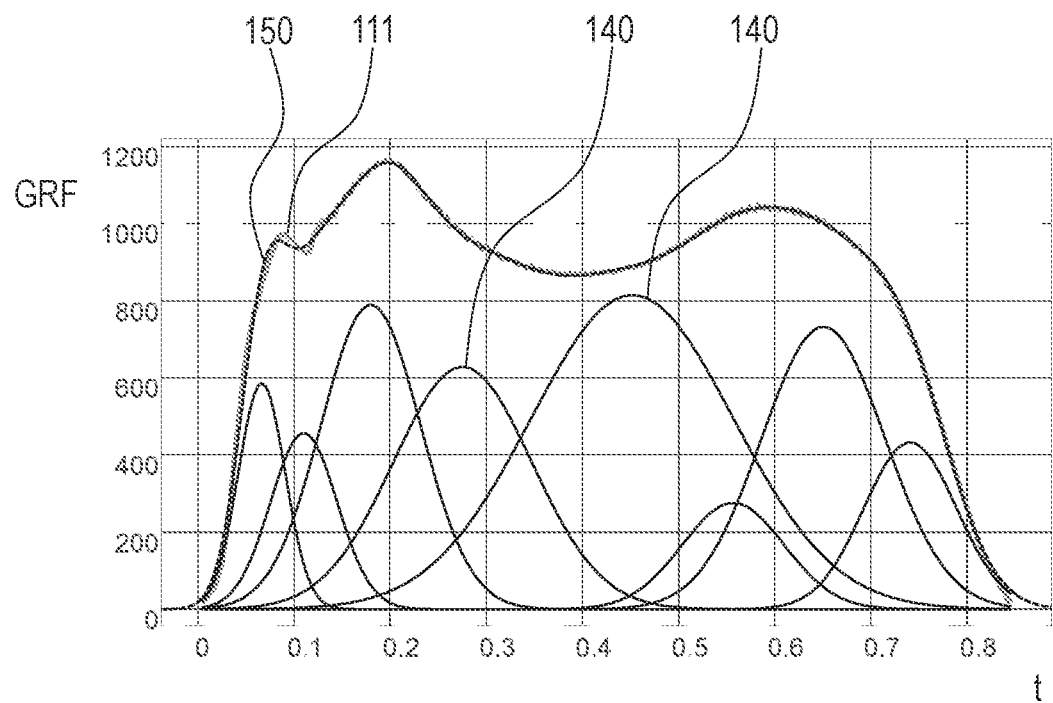

With reference to FIG. 2, which shows in a diagram an exemplary ground reaction force curve 111 provided as data by the force measuring device 110, an exemplary operation of the gait analysis system 100 is explained below. In the diagram, the vertical axis represents the ground reaction force, which is therefore denoted GRF. The horizontal axis of the diagram represents time, which is therefore denoted by t.

First, the data obtained from the force measuring device 110 is normalized to the body weight of the person whose gait is to be analyzed. This can be done using weight data, for example, automatically or by input via a user interface or the like.

A first approximation of the ground reaction force curve 111 is then determined by means of the evaluation device 130, for which purpose a plurality of first approximation functions 140 is selected. In the exemplary embodiment shown in FIG. 2, exactly eight first approximation functions 140 have been selected for the clinical gait analysis. The first approximation functions 140 represent normal distributions or Gaussian functions, differing from each other and are defined by a set of coefficients 141, 142, 143, which represent a maximum value, a position, e.g. relative to an X-axis, in particular e.g. the position of a maximum value and/or a mean value, and a width of the respective first approximation function 140 (cf. FIG. 3). The first approximation functions 140 are selected in an iterative procedure by determining a sum function and its deviation from the ground reaction force curve 111 in each iteration step until the deviation reaches a predetermined termination criterion and the corresponding first approximation function for the first approximation is determined therefrom. In this embodiment example, residuals, i.e. the sum of the deviations squared, are determined from the sum function of the first approximation functions 140. If these deviations of a first approximation function 140 are too large, another one is chosen. Preferably, this is repeated iteratively until a minimum of the residuals is given and the quality of the function reaches an $R^2$ of, for example, at least 0.8. Preferably, the combination of the minimum of the residuals and the values of the $R^2$ represents the termination criterion for the iterative procedure. Once the first approximation functions 140 for the first approximation have thus been found, the coefficients 141, 142, 143 of all first approximation functions 140 are collected and/or combined in a coefficient pool 144 (see FIG. 1), whereby in this exemplary embodiment 8·3=24 coefficients are included in the coefficient pool 144.

Based on the coefficients 141, 142, 143 of the first approximation functions 140 included herein in the coefficient pool 144, a second approximation of the ground reaction force curve 111 is determined by a second approximation function 150. This is done by feeding the coefficients 141, 142, 143 to the input layer of the neural network of the evaluation device 130. Preferably, the second approximation function 150 is a sum function of the first approximation functions and is formed from part or all of the coefficients 141, 142, 143 of the coefficient pool 144. In FIG. 2, the second approximation function 150 is shown as a dashed line, and a comparison with the ground reaction force curve 111 shows that the second approximation describes it extremely accurately, as they are approximately congruent. Optionally, the coefficients 141, 142, 143 of the coefficient pool 144 used to form the second approximation function 150 are compared in advance to the data set 135 which includes a plurality of already classified comparison ground reaction force trajectories. This comparison is used to determine whether it is statistically possible to actually distinguish a predetermined class, such as a particular walking style. Thus, the coefficients 141, 142, 143 of the coefficient pool 144 are pre-validated. Then, the second approximation function 150 is formed from the coefficients 141, 142, 143 validated using the data set 135 in an iterative procedure and the second approximation is assigned to a class. In this procedure, the coefficients 141, 142, 143 are combined with each other until a termination criterion is reached, which may be, for example, minimization of a residual. From this, the approximated ground reaction force curve 111 may have an expression of the coefficients 141, 142, 143 that can be assigned to a respective class. As a result, a description and classification of the ground reaction force curve 111 is output by the output layer of the neural network. This result allows for an objective and valid gait analysis.

Figure 3:
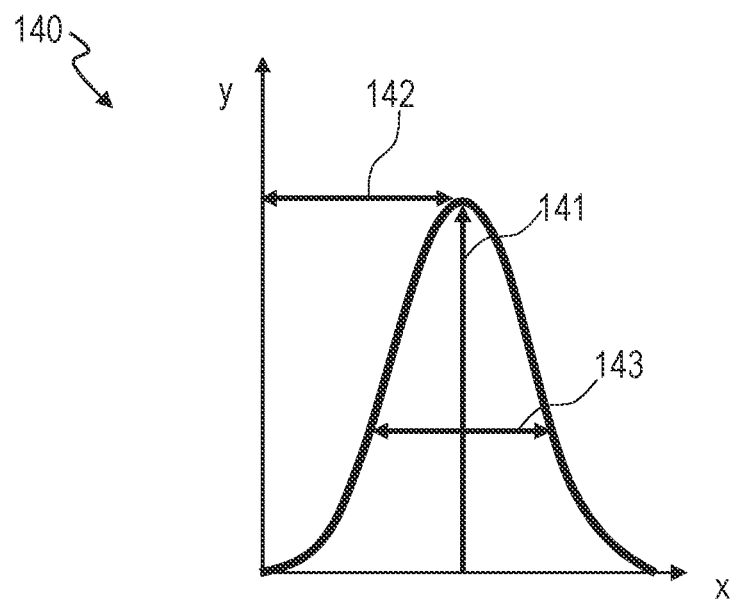

FIG. 3 shows, for better illustration, an exemplary first approximation function defined by the three coefficients, namely the maximum value 141, the position, 142 and the width 143.

Figure 4:
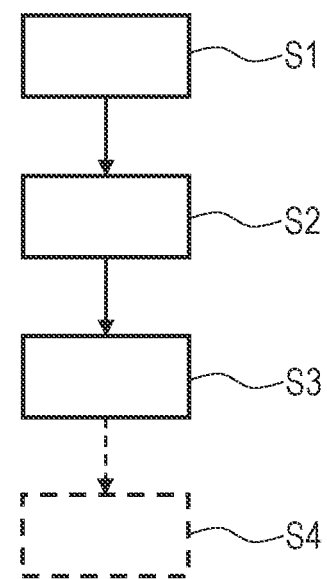

With reference to FIG. 4, which shows a flow chart, a method for gait analysis according to the invention will be explained below. First, in a step S1, data comprising the ground reaction force curve 111 is obtained from the force measuring device 110. Then, in a step S2, a first approximation of the ground reaction force curve 111 is determined by one or more of the first approximation functions 140 defined by the coefficients 141, 142, 143. In a step S3, a second approximation of the ground reaction force profile 111 is determined by the second approximation function 150 formed based on the coefficients 141, 142, 143 of the one or more first approximation functions 140. In an optional step S4, the coefficients 141, 142, 143 are compared to at least one predetermined data set 135 comprising a plurality of classified ground reaction force trajectories. Based on this comparison, it is validated whether the coefficients 141, 142, 143 enable the second approximation. Further optionally, the coefficients 141, 142, 143 are associated with a predetermined gait behavior, gait abnormality, and/or other foot-ground interaction by comparison with the data set 135.

Although the present invention has been described above with reference to particular embodiments, it is not limited thereto, but is modifiable in a variety of ways. In particular, the present invention can be altered or modified in a variety of ways without departing from the essence of the invention.

It should also be noted that "comprising" and "comprising" do not exclude other elements or steps, and "one" or "a" do not exclude a plurality.

It should further be noted that features or steps that have been described with reference to any of the above embodiments may also be used in combination with other features or steps of other embodiments described above. Reference signs in the claims are not to be regarded as limitations.

LIST OF REFERENCE SIGNS 100 gait analysis system
110 force measuring device
111 ground reaction force curve
130 electronic evaluation device
131 processor
132 memory
133 computer program element
134 database
135 predetermined data set
140 first approximation function
141 first coefficient (e.g. maximum value)
142 second coefficient (e.g. position)
143 third coefficient (e.g. width)
144 coefficient pool
150 second approximation function

The invention claimed is:
1. A method for gait analysis, comprising:
obtaining data including a ground reaction force curve from a force measuring device,
determining a first approximation of the ground reaction force curve by at least a first approximation function defined by a set of coefficients, and
determining a second approximation of the ground reaction force curve by a second approximation function formed on the basis of the set of coefficients of the at least one first approximation function, wherein the at least one set of coefficients is combined into a coefficient pool from which individual coefficients can be combined to form the second approximation function;

providing a neural network arranged to obtain the at least one set of coefficients as an input variable and to generate a class information as an output variable;

wherein the at least one set of coefficients comprises a maximum value, a position, and a width of the first approximation function;

wherein the output variable is one of the following: a respective sport, in a medical setting a respective pathology or stage of impairment.

2. The method of claim 1, wherein a plurality of mutually different first approximation functions defined by the respective set of coefficients are determined.

3. The method according to claim 1, wherein at least two first approximate functions are iteratively selected, from which a sum function and its deviation from the ground reaction force curve are determined in a respective iteration step until the deviation reaches a predetermined termination criterion and the corresponding first approximate function for the first approximation is determined therefrom.

4. The method according to claim 1, wherein the coefficients forming the second approximation function are compared in advance with at least one predetermined data set comprising a plurality of classified ground reaction force trajectories and validated therefrom whether the coefficients enable the second approximation.

5. The method according to claim 4, wherein the second approximation function is iteratively formed from the validated coefficients and the second approximation is assigned to a class.

6. The method according to claim 1, wherein the first approximation function is a normal distribution or Gaussian function.

7. The method according to claim 1, wherein the second approximation function is a sum function of the at least one first approximation function.

8. The method according to claim 1, wherein a number of the determined first approximation function is set between 1 and 20.

9. A gait analysis system, comprising:
a force measuring device configured to detect a ground reaction force, an electronic evaluation device configured to:
approximate, from the detected ground reaction force, a ground reaction force curve by at least a first approximation function defined by a set of coefficients, and
further approximate the ground reaction force curve by a second approximation function formed on the basis of the set of coefficients, and
a database adapted to associate a combination of coefficients forming the second approximation function with a predetermined gait, a gait abnormality, and/or another foot- ground interaction;
further comprising at least one neural network adapted to receive the coefficients as input and to generate class information as output;
wherein the coefficients comprise a maximum value, a position and a width of the first approximation function;
wherein the class information is one of the following: a respective sport, in a medical setting a respective pathology, or stage of impairment.

10. A non-transitory computer readable medium comprising program element which, when executed by means of a processor of an electronic evaluation device, causes the evaluation device to perform the following steps:
obtaining data including a ground reaction force curve from a force measuring device,
determining a first approximation of the ground reaction force curve by at least a first approximation function defined by a set of coefficients, and
determining a second approximation of the ground reaction force curve by a second approximation function formed on the basis of the set of coefficients of the first approximation function,
wherein the at least one set of coefficients is combined into a coefficient pool from which individual coefficients can be combined to form the second approximation function;
providing a neural network arranged to obtain the at least one set of coefficients as an input variable and to generate a class information as an output variable;
wherein the at least one set of coefficients comprises a maximum value, a position and a width of the first approximation function;
wherein the output variable is one of the following: a respective sport, in a medical setting a respective pathology or stage of impairment.

* * * * *

UNITED STATES PATENT AND TRADEMARK OFFICE
CERTIFICATE OF CORRECTION

PATENT NO. : 12,109,016 B2
APPLICATION NO. : 17/255904
DATED : October 8, 2024
INVENTOR(S) : Thomas Ertelt Page 1 of 1

It is certified that error appears in the above-identified patent and that said Letters Patent is hereby corrected as shown below:

On the Title Page

Item (71) Applicant, "Heidelberg" should be --Potsdam--.

Item (57) Abstract, Line 5, "curve performed" should be --curve is performed--.

Signed and Sealed this
Twenty-sixth Day of November, 2024

Katherine Kelly Vidal
*Director of the United States Patent and Trademark Office*